(12) United States Patent
Moffat et al.

(10) Patent No.: US 7,012,076 B2
(45) Date of Patent: Mar. 14, 2006

(54) BICYCLIC AMINE DERIVATIVES AS INHIBITORS OF CLASS 1 RECEPTOR TYROSINE KINASES

(75) Inventors: David Festus Charles Moffat, Berkshire (GB); Peter David Davis, Oxfordshire (GB)

(73) Assignee: Celltech R&D Limited, Berkshire (GB)

( * ) Notice: Subject to any disclaimer, the term of this patent is extended or adjusted under 35 U.S.C. 154(b) by 159 days.

(21) Appl. No.: 10/239,941

(22) PCT Filed: Mar. 29, 2001

(86) PCT No.: PCT/GB01/01438

§ 371 (c)(1),
(2), (4) Date: Feb. 4, 2003

(87) PCT Pub. No.: WO01/72720

PCT Pub. Date: Oct. 4, 2001

(65) Prior Publication Data

US 2003/0153755 A1    Aug. 14, 2003

(30) Foreign Application Priority Data

Mar. 29, 2000 (GB) .................... 0007657

(51) Int. Cl.
C07D 239/94 (2006.01)
A61K 31/505 (2006.01)

(52) U.S. Cl. .................... 514/266.4; 544/293
(58) Field of Classification Search ........... 544/293; 514/266.4
See application file for complete search history.

(56) References Cited

U.S. PATENT DOCUMENTS 2,473,931 A * 6/1949 Wolf .................... 544/292

FOREIGN PATENT DOCUMENTS

| GB | 920 019 | 8/1964 |
| GB | 1 144 022 | 3/1966 |
| GB | 1092737 | * 11/1967 |
| WO | WO 96/09294 | 3/1996 |

OTHER PUBLICATIONS

Wolf, CAPLUS Abstract 43:38995, 1949.*
Rodda, CAPLUS Abstract 51:12955, 1957.*
Mead Johnson & Co., CAPLUS Abstract 59:21813, 1963.*
Biochemie, CAPLUS Abstract 66:65504, 1967.*
Skwarski et al., CAPLUS Abstract 107:198240, 1987.*
Iwai et al., CAPLUS Abstract 131:315796, 1999.*
Jost et al., Medline Abstract (J Invest Dermatol 112(4):443-9), 1999.*
Simone, Oncology: Introduction, Cecil Textbook of Medicine, 20th Edition, vol. 1, pp. 1004-1010, 1996.*
Traxler, Protein Tyrosine kinase inhibitors in cancer treatment, Exp. Opin. Ther. Patents, 7(6):571-588, 1997.*
Biniecki, S., et al., "Synthesis of some sulfaniloamido derivatives of quinoline," *Acta. Pol. Pharm.*, 1965, 22(2), 103-106.
Carraway, K.L., et al., "A neu acquaintance for ErbB3 and ErbB4: a role for receptor heterodimerization in growth signaling," *Cell*, Jul. 15, 1994, 78, 5-8.
Chan, C., et al., "The role of protein tyrosine kinases and protein tyrosine phosphatases in T cell antigen receptor signal transduction," *Ann. Rev. Immunol.*, 1994, 12, 555-592.
Chemical Abstracts Service, 181. Cesare Pellerano. —Sintesi di sulfamidici chinolinici—notal, *Ann. Chim.*, XP002169371, 53(12), 1963, 1850-1859.
English, J.P., et al., "Studies in chemotherapy. XIV. Antimalarials. The synthesis of substituted metanilamides and related compounds," *J. Amer. Chem. Soc.*, XP002169372, Jun. 1946, 68, 1039-1049.

(Continued)

*Primary Examiner*—Deepak Rao
(74) *Attorney, Agent, or Firm*—Woodcock Washburn LLP

(57) ABSTRACT

Fused bicyclic amines of formula (1) are described wherein Ar is an aryl or heteroaryl group; Y is a —S(O$_2$)— or —C(O)— group; R$^1$ is a hydrogen or halogen atom or an alkyl, haloalkyl, alkoxy, haloalkoxy or cyano group; X is a nitrogen atom or a C(R$^{1a}$) group where R$^{1a}$ is as defined for R$^1$ and may be the same or different; W and Z are each a carbon atom and together with U form an optionally substituted five- or six-membered monocyclic aromatic or heteroaromatic group; and the salts, solvates, hydrates and N-oxides thereof. The compounds are able to inhibit the activity of Class 1 receptor tyrosine kinases and are of use in the prophylaxis and treatment of hyperproliferative disorders such as cancer, psoriasis, restenosis, atherosclerosis and fibrosis.

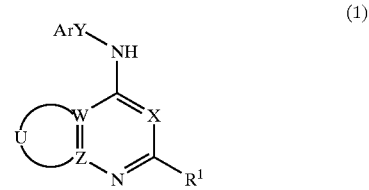

(1)

4 Claims, No Drawings

OTHER PUBLICATIONS

Geissler, J.F., et al., "Thiazolidine-Dones: biochemical and biological activity of a novel class of tyrosine protein kinase inhibitors," *J. Biol. Chem.*, Dec. 25, 1990, 265(36), 22255-22261.

Green, T. W., in Protective Groups in Organic Synthesis, *J. Wiley & Sons*, 1991.

Hanks, S.K., et al., "the eukaryotic protein kinase superfamily: kinase (catalytic) domain structure and classification," *FASEB J.*, May 1995, 9, 576-596.

Iwashita, S., et al., "Signal transduction system for growth factor receptors associated with tyrosine kinase activity: epidermal growth factor receptor signaling and its regulation," *Cellular Signalling*, 1992, 4(2), 123-132.

Pyóips, M.B., et al. Beilstein Institute for Organic Chemistry, *Zh. Obshch. Khim.*, 1994, XP002169373, 14, 857-861 (No English abstract).

* cited by examiner

BICYCLIC AMINE DERIVATIVES AS INHIBITORS OF CLASS 1 RECEPTOR TYROSINE KINASES

This application is a 371 of PCT/GB01/01438 filed Mar. 29, 2001.

This invention relates to a series of fused bicyclic amines, to processes for their preparation, to pharmaceutical compositions containing them, and to their use in medicine.

Regulation of protein tyrosine phosphorylation by tyrosine kinases is essential for the regulation of cell growth and differentiation [Hanks, S. K. Hunter T., FASEB J. 9, 576–596 (1995)]. The tyrosine kinases may belong to one of two general classes, namely, the transmembrane growth factor receptor tyrosine kinases (EGFr, c-ErbB-2, PDGF, KDR, etc.) [Iwashita S. and Kobayashi M., Cellular Signalling, 4, 123–132 (1992)] and cytoplasmic nonreceptor tyrosine kinases (src, Ick, ZAP70 etc.) [Chan C. et al, Ann. Rev. Immunol. 12, 555–592 (1994)]. In the case of receptor tyrosine kinases, growth factors, such as epidermal growth factor (EGF), bind to the extracellular binding domain of the receptor, leading to receptor dimerisation and activation of the receptor kinase domain leading to autophosphorylation. This initiates a signal transduction cascade leading ultimately to proliferation. Considerable evidence has emerged to implicate Class 1 receptor tyrosine kinases, such as EGFr and c-ErbB-2 in the progression of several human cancers [Carraway K. & Cantley L, Cell, 78, 5–8 (1994)]. In particular, increased levels of EGFr and c-Erb-2 occur in a significant percentage of breast and non-small cell lung carcinomas in which overexpression correlates with shortened survival times and increased relapse rates. The ability of these receptors to undergo homo- and heterodimerisation leads to an intensification of the transforming signal and contributes to the complexity of the EGFr family signalling network. The disruption of the normal functions of these tyrosine kinases has been implicated in a number of other hyperproliferative disorders such as psoriasis, restenosis, atherosclerosis and fibrosis of the liver and kidney.

The present invention relates to a series of fused bicyclic amines that are able to inhibit the activity of Class I receptor tyrosine kinases, thus permitting a new therapeutic approach for disease states such as cancer, psoriasis, restenosis, atherosclerosis and fibrosis.

Thus according to one aspect of the invention we provide a compound of formula (1):

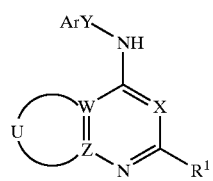

wherein
Ar is an aryl or heteroaryl group;
Y is a —S($O_2$)— group;
$R^1$ is a hydrogen or halogen atom or an alkyl, haloalkyl, alkoxy, haloalkoxy or cyano group;
X is a nitrogen atom or a C($R^{1a}$) group where $R^{1a}$ is as defined for $R^1$ and may be the same or different;
W and Z is each a carbon atom and together with U form an optionally substituted five- or six-membered monocyclic aromatic or heteroaromatic group;

and the salts, solvates, hydrates and N-oxides thereof.

Aryl groups represented by the group Ar in compounds of formula (1) include for example mono- or bicyclic-$C_{6-12}$ optionally substituted aromatic groups, for example optionally substituted phenyl, 1- or 2-naphthyl, or indenyl groups.

Heteroaryl groups represented by Ar include for example $C_{1-9}$ optionally substituted heteroaromatic groups containing for example one, two, three or four heteroatoms selected from oxygen, sulphur or nitrogen atoms. In general, the heteroaromatic groups may be for example monocyclic or bicyclic heteroaromatic groups. Monocyclic heteroaromatic groups include for example five- or six-membered heteroaromatic groups containing one, two, three or four heteroatoms selected from oxygen, sulphur or nitrogen atoms. Bicyclic heteroaromatic groups include for example nine- to thirteen-membered heteroaromatic groups containing one, two or more heteroatoms selected from oxygen, sulphur or nitrogen atoms.

The aryl or heteroaryl groups represented by Ar may be attached to the group Y through any available ring carbon or heteroatom as appropriate.

Particular examples of heteroaromatic groups represented by Ar include optionally substituted pyrrolyl, furyl, thienyl, imidazolyl, N-methylimidazolyl, N-ethyl-imidazolyl, oxazolyl, isoxazolyl, thiazolyl, isothiazolyl, pyrazolyl, 1,2,3-triazolyl, 1,2,4-triazolyl, 1,2,3-oxadiazolyl, 1,2,4-oxadiazolyl, 1,2,5-oxadiazolyl, 1,3,4-oxadiazolyl, 1,3,4-thiadiazole, pyridyl, pyrimidinyl, pyridazinyl, pyrazinyl, 1,3,5-triazinyl, 1,2,4-triazinyl, 1,2,3-triazinyl, benzofuryl, isobenzofuryl, benzothienyl, benzotriazolyl, isobenzothienyl, indolyl, isoindolyl, benzimidazolyl, imidazo[1,2-a]pyridyl, benzothiazolyl, benzoxazolyl, quinazolinyl, naphthyridinyl, pyrido[3,4-b]pyridyl, pyrido[3,2-b]pyridyl, pyrido[4,3-b]pyridyl, quinolinyl, isoquinolinyl, tetrazolyl, 5,6,7,8-tetrahydroquinolinyl and 5,6,7,8-tetrahydroisoquinolinyl.

Optional substituents present on the aryl or heteroaryl groups represented by Ar include one, two, three or more groups, each represented by the group $R^2$. The substituent $R^2$ may be selected from an atom or group $R^3$ or -$Alk^1(R^3)_n$, where $R^3$ is a halogen atom, or an amino (—$NH_2$), substituted amino, nitro, cyano, hydroxyl (—OH), substituted hydroxyl, formyl, carboxyl (—$CO_2H$), esterified carboxyl, thiol (—SH), substituted thiol, —$COR^4$ [where $R^4$ is an -$Alk^1(R^3)_n$, aryl or heteroaryl group], —$CSR^4$, —$SO_3H$, —$SO_2R^4$ —$SO_2NH_2$, —$SO_2NHR^4$, —$SO_2N(R^4)_2$, —$CONH_2$, —$CSNH_2$, —$CONHR^4$, —$CSNHR^4$, —$CON(R^4)_2$, —$CSN(R^4)_2$, —$NHSO_2H$, —$NHSO_2R^4$, —$N(SO_2R^4)_2$, —$NHSO_2NH_2$, —$NHSO_2NHR^4$ —$NHSO_2N(R^4)_2$, —$NHCOR^4$, —$NHCSR^4$ —$NHC(O)OR^4$, aryl or heteroaryl group; $Alk^1$ is a straight or branched $C_{1-6}$alkylene, $C_{2-6}$alkenylene or $C_{2-6}$alkynylene chain, optionally interrupted by one, two or three —O— or —S— atoms or —S(O)$_p$ [where p is an integer 1 or 2] or —N($R^5$)— groups [where $R^5$ is a hydrogen atom or $C_{1-6}$alkyl, e.g. methyl or ethyl group]; and n is zero or an integer 1, 2 or 3.

When in the group -$Alk^1(R^3)_n$, n is an integer 1, 2 or 3, it is to be understood that the substituent or substituents $R^3$ may be present on any suitable carbon atom in -$Alk^1$. Where more than one $R^3$ substituent is present these may be the same or different and may be present on the same or different atom in -$Alk^1$. Clearly, when n is zero and no substituent $R^3$ is present the alkylene, alkenylene or alkynylene chain represented by $Alk^1$ becomes an alkyl, alkenyl or alkynyl group.

When $R^3$ is a substituted amino group it may be for example a group —$NHR^4$ [where $R^4$ is as defined above] or a group —$N[R^4]_2$ wherein each $R^4$ group is the same or different.

When $R^3$ is a halogen atom it may be for example a fluorine, chlorine, bromine, or iodine atom.

When $R^3$ is a substituted hydroxyl or substituted thiol group it may be for example —$OR^4$, —$SR^4$ or —$SC(=NH)NH_2$ group respectively.

Esterified carboxyl groups represented by the group $R^3$ include groups of formula —$CO_2Alk^2$ wherein $Alk^2$ is a straight or branched, optionally substituted $C_{1-8}$alkyl group such as a methyl, ethyl, n-propyl, i-propyl, n-butyl, i-butyl, s-butyl or t-butyl group; a $C_{6-12}$aryl$C_{1-8}$alkyl group such as an optionally substituted benzyl, phenylethyl, phenylpropyl, 1-naphthylmethyl or 2-naphthylmethyl group; a $C_{6-12}$aryl group such as an optionally substituted phenyl, 1-naphthyl or 2-naphthyl group; a $C_{6-12}$aryloxy$C_{1-8}$-alkyl group such as an optionally substituted phenyloxymethyl, phenyloxyethyl, 1-naphthyloxymethyl, or 2-naphthyloxymethyl group; an optionally substituted $C_{1-8}$alkanoyloxy$C_{1-8}$alkyl group, such as a pivaloyloxymethyl, propionyloxyethyl or propionyloxypropyl group; or a $C_{6-12}$aroyloxy$C_{1-8}$alkyl group such as an optionally substituted benzoyloxyethyl or benzoyl-oxypropyl group. Optional substituents present on the $Alk^2$ group include $R^8$ substituents described above.

When $Alk^1$ is present in or as a substituent $R^2$ it may be for example a methylene, ethylene, n-propylene, i-propylene, n-butylene, i-butylene, s-butylene, t-butylene, ethenylene, 2-propenylene, 2-butenylene, 3-butenylene, ethynylene, 2-propynylene, 2-butynylene or 3-butynylene chain, optionally interrupred by one, two, or three —O— or —S—, atoms or —S(O)—, —S(O)$_2$— or —N($R^5$)— groups.

Aryl or heteroaryl groups represented by the groups $R^3$ or $R^4$ include mono- or bicyclic optionally substituted $C_{6-12}$ aromatic or $C_{1-9}$ heteroaromatic groups as described above for the group Ar. The aromatic and heteroaromatic groups may be attached to the remainder of the compound of formula (1) by any carbon or hetero e.g. nitrogen atom as appropriate.

Particularly useful atoms or groups represented by $R^2$ include fluorine, chlorine, bromine or iodine atoms, or $C_{1-6}$alkyl, e.g. methyl or ethyl, $C_{1-6}$hydroxyalkyl, e.g. hydroxymethyl or hydroxyethyl, $C_{1-6}$alkylthiol e.g. methylthiol or ethylthiol, $C_{1-6}$alkoxy, e.g. methoxy or ethoxy, $C_{5-7}$cycloalkoxy, e.g. cyclopentyloxy, halo$C_{1-6}$alkyl, e.g. trifluoromethyl, halo$C_{1-6}$alkoxy e.g. trifluoromethoxy, $C_{1-6}$alkylamino, e.g. methylamino or ethylamino, amino (—$NH_2$), amino$C_{1-6}$alkyl, e.g. aminomethyl or aminoethyl, $C_{1-6}$dialkylamino, e.g. dimethylamino or diethylamino, imido, such as phthalimido or naphthalimido, e.g. 1,8-naphthalimido, 1,1,3-trioxobenzo-[d]thiazolidino, nitro, cyano, hydroxyl (—OH), formyl [HC(O)—], carboxyl (—$CO_2H$), —$CO_2Alk^2$ [where $Alk^2$ is as defined above], $C_{1-6}$ alkanoyl e.g. acetyl, thiol (—SH), thio$C_{1-6}$alkyl, e.g. thiomethyl or thioethyl, —$SC(=NH)NH_2$, sulphonyl (—$SO_3H$), $C_{1-6}$alkylsulphonyl, e.g. methylsulphonyl, aminosulphonyl (—$SO_2NH_2$), $C_{1-6}$alkylaminosulphonyl, e.g. methylaminosulphonyl or ethylaminosulphonyl, $C_{1-6}$dialkylaminosulphonyl, e.g. dimethylaminosulphonyl or diethylaminosulphonyl, phenylaminosulphonyl, carboxamido (—$CONH_2$), $C_{1-6}$alkylaminocarbonyl, e.g. methylaminocarbonyl or ethylaminocarbonyl, $C_{1-6}$dialkylaminocarbonyl, e.g. dimethylaminocarbonyl or diethylaminocarbonyl, sulphonylamino (—$NHSO_2H$), $C_{1-6}$alkylsulphonylamino, e.g. methylsulphonylamino or ethylsulphonylamino, $C_{1-6}$dialkylsulphonylamino, e.g. dimethylsulphonylamino or diethylsulphonylamino, optionally substituted phenylsulphonylamino, e.g. 2-, 3- or 4-substituted phenylsulphonylamino such as 2-nitrophenylsulphonylamino, aminosulphonylamino (—$NHSO_2NH_2$), $C_{1-6}$alkylaminosulphonylamino, e.g. methylaminosulphonylamino or ethylaminosulphonylamino, $C_{1-6}$dialkylaminosulphonylamino, e.g. dimethylamino-sulphonylamino or diethylaminosulphonylamino, phenylaminosulphonylamino, $C_{1-6}$alkanoylamino, e.g. acetylamino, $C_{1-6}$alkanoylamino$C_{1-6}$alkyl, e.g. acetylaminomethyl, $C_{1-6}$alkoxycarbonylamino, e.g. methoxycarbonylamino, ethoxycarbonylamino or t-butoxycarbonylamino or optionally substituted benzyloxy groups.

Where desired, two $R^2$ substituents may be linked together to form a cyclic group such as a cyclic ether, e.g. a $C_{1-6}$alkylenedioxy group such as methylenedioxy or ethylenedioxy.

It will be appreciated that where two or more $R^2$ substituents are present, these need not necessarily be the same atoms and/or groups.

When W, Z and U form an optionally substituted five- or six-membered monocyclic aromatic or heteroaromatic group the group may be for example an optionally substituted phenyl or five- or six-membered monocyclic heteroaromatic group containing one or two nitrogen, oxygen and/or sulphur atoms. Particular examples of such groups include optionally substituted pyrazolyl, pyridyl and pyrimidinyl groups. In general, the optional substituents which may be present on aromatic or heteroaromatic groups represented by W, Z and U together, include one to four $R^2$ substituents where $R^2$ is as defined previously in connection with Ar aryl and heteroaryl groups.

Halogen atoms represented by the groups $R^1$ and $R^{1a}$ in compounds of formula (1) include fluroine, chlorine, bromine and iodine atoms.

Alkyl groups represented by $R^1$ and $R^{1a}$ include $C_{1-6}$alkyl groups, e.g. $C_{1-4}$alkyl such as methyl and ethyl groups.

Alkoxy groups represented by $R^1$ and $R^{1a}$ include $C_{1-6}$alkoxy groups, e.g. $C_{1-6}$alkoxy such as methoxy and ethoxy.

Haloalkyl and haloalkoxy groups represented by $R^1$ and $R^{1a}$ include those alkyl and alkoxy groups just mentioned in which one or more carbon atoms is substituted by one, two or three halogen atoms, e.g. fluorine or chlorine atoms. Particular examples include —$CF_3$, —$CCl_3$, —$CHF_2$, —$CHCl_2$, —$CH_2CF_3$, —$CH(CF_3)_2$, —$CH_2CH(CF_3)_2$, —$C(CF_3)_2CH_3$, and the corresponding alkoxy groups.

The presence of certain substituents in the compounds of formula (1) may enable salts of the compounds to be formed. Suitable salts include pharmaceutically acceptable salts, for example acid addition salts derived from inorganic or organic acids, and salts derived from inorganic and organic bases.

Acid addition salts include hydrochlorides, hydrobromides, hydroiodides, alkylsulphonates, e.g. methanesulphonates, ethanesulphonates, or isethionates, arylsulphonates, e.g. p-toluenesulphonates, besylates or napsylates, phosphates, sulphates, hydrogen sulphates, acetates, trifluoroacetates, propionates, citrates, maleates, fumarates, malonates, succinates, lactates, oxalates, tartrates and benzoates.

Salts derived from inorganic or organic bases include alkali metal salts such as sodium or potassium salts, alkaline earth metal salts such as magnesium or calcium salts, and organic amine salts such as morpholine, piperidine, dimethylamine or diethylamine salts.

Particularly useful salts of compounds according to the invention include pharmaceutically acceptable salts, especially acid addition pharmaceutically acceptable salts.

It will be appreciated that where compounds of formula (1) exist as geometrical isomers and/or enantiomers or diasteromers then the invention extends to all such isomers of the compounds of formula (1), and to mixtures thereof, including racemates.

One particularly useful group of compounds according to the invention is that wherein Ar is an optionally substituted aromatic group. Particularly useful compounds of this type are those wherein Ar is an optionally substituted phenyl group. In compounds of this type Ar may be in particular a phenyl group or a phenyl group substituted by one or two $R^2$ groups as defined herein.

In a further preference, W and Z together with U form an optionally substituted phenyl group. Particularly useful compounds of this type include compounds of formula (1a):

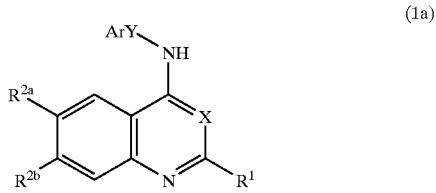

(1a)

wherein $R^{2a}$ and $R^{2b}$, which may be the same or different is each a hydrogen atom or an atom or group $R^2$ as generally and specifically defined previously, Ar, Y, X and $R^1$ are as generally and specifically defined previously, and the salts, solvates, hydrates and N-oxides thereof.

In compounds of formula (1a), Ar is in particular an optionally substituted phenyl group, Y is —S($O_2$)— and X is a C($R^{1a}$) group where $R^{1a}$ is a cyano group, or X is a nitrogen atom. X is most preferably a nitrogen atom.

In compounds of formulae (1) and (1a) $R^1$ is preferably a hydrogen atom.

Particularly preferred optional substituents which may be present on phenyl rings represented by Ar in compounds of formula (1a) include halogen atoms, especially fluorine, chlorine, bromine or iodine atoms, or cyano, $C_{1-6}$alkoxy e.g. methoxy or ethoxy, or $C_{1-6}$alkyl groups e.g. methyl or ethyl groups.

Especially preferred optional substituents include those substituents just described located at the 3- or most especially 2-position of the phenyl ring respresented by Ar in compounds of formula (1a).

In one preferred class of compounds of formula (1a) $R^{2a}$ or $R^{2b}$ is a substituent $R^2$ as hereinbefore defined other than a hydrogen atom.

In another preferred class of compounds of formula (1a) $R^{2a}$ and $R^{2b}$ is each a substituent $R^2$ as hereinbefore defined other than a hydrogen atom.

In another preferred class of compounds of formula (1a) $R^{2a}$ and $R^{2b}$ which may be the same or different is each a $C_{1-6}$alkoxy group, especially a methoxy or ethoxy group.

Particularly useful compounds according to the invention include:
2-Bromo-N-(6,7-dimethoxyquinazolin-4-yl)benzenesulphonamide;
N-(6,7-Dimethoxyquinazolin4-yl)-2-iodobenzenesulphonamide;
2-Cyano-N-(6,7-dimethoxyquinazolin-4-yl)benzenesulphonamide;
4-Bromo-N-(6,7-dimethoxyquinazolin-4-yl)benzenesulphonamide;
2-Chloro-N-(6,7-dimethoxyquinazolin-4-yl)benzenesulphonamide;
3-Chloro-N-(6,7-dimethoxyquinazolin-4-yl)benzenesulphonamide;
4-Chloro-N-(6,7-dimethoxyquinazolin-4-yl)benzenesulphonamide;
N-(6,7-Dimethoxyquinazolin4-yl)4-methoxybenzenesulphonamide;
N-(6,7-Dimethoxyquinazolin4-yl)4-methylbenzenesulphonamide;

and the salts, solvates and hydrates thereof.

Compounds according to the invention are potent and selective inhibitors of Class I receptor tyrosine kinases, especially EGFr kinase as demonstrated by differential inhibition of this enzyme when compared to inhibition of other protein kinases such as $p56^{lck}$ kinase, protein kinase C, KDR kinase and FGFr2 kinase. The ability of the compounds to act in this way may be simply determined by the tests described in the Examples hereinafter.

The compounds according to the invention are thus of particular use in the prophylaxis and treatment of diseases in which inappropriate Class I receptor tyrosine kinase action plays a role, for example in hyperproliferative disorders such as tumours, psoriasis, restenosis following angioplasty, atherosclerosis, and fibrosis e.g. of the liver and kidney.

For the prophylaxis or treatment of disease the compounds according to the invention may be administered as pharmaceutical compositions, and according to a further aspect of the invention we provide a pharmaceutical composition which comprises a compound of formula (1) together with one or more pharmaceutically acceptable carriers, excipients or diluents.

Pharmaceutical compositions according to the invention may take a form suitable for oral, buccal, parenteral, nasal, topical or rectal administration, or a form suitable for administration by inhalation or insufflation.

For oral administration, the pharmaceutical compositions may take the form of, for example, tablets, lozenges or capsules prepared by conventional means with pharmaceutically acceptable excipients such as binding agents (e.g. pregelatinised maize starch, polyvinylpyrrolidone or hydroxypropyl methylcellulose); fillers (e.g. lactose, microcrystalline cellulose or calcium hydrogen phosphate); lubricants (e.g. magnesium stearate, talc or silica); disintegrants (e.g. potato starch or sodium glycollate); or wetting agents (e.g. sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents, emulsifying agents, non-aqueous vehicles and preservatives. The preparations may also contain buffer salts, flavouring, colouring and sweetening agents as appropriate.

Preparations for oral administration may be suitably formulated to give controlled release of the active compound.

For buccal administration the compositions may take the form of tablets or lozenges formulated in conventional manner.

The compounds for formula (1) may be formulated for parenteral administration by injection e.g. by bolus injection or infusion. Formulations for injection may be presented in unit dosage form, e.g. in glass ampoule or multi dose containers, e.g. glass vials. The compositions for injection may take such forms as suspensions, solutions or emulsions in oily or aqueous vehicles, and may contain formulatory agents such as suspending, stabilising, preserving and/or dispersing agents. Alternatively, the active ingredient may be in powder form for constitution with a suitable vehicle, e.g. sterile pyrogen-free water, before use.

In addition to the formulations described above, the compounds of formula (1) may also be formulated as a depot preparation. Such long acting formulations may be administered by implantation or by intramuscular injection.

For nasal administration or administration by inhalation, the compounds for use according to the present invention are conveniently delivered in the form of an aerosol spray presentation for pressurised packs or a nebuliser, with the use of suitable propellant, e.g. dichlorodifluoromethane, trichlorofluoromethane, dichlorotetrafluoroethane, carbon dioxide or other suitable gas or mixture of gases.

The compositions may, if desired, be presented in a pack or dispenser device which may contain one or more unit dosage forms containing the active ingredient. The pack or dispensing device may be accompanied by instructions for administration.

The quantity of a compound of the invention required for the prophylaxis or treatment of a particular condition will vary depending on the compound chosen, and the condition of the patient to be treated. In general, however, daily dosages may range from around 100 ng/kg to 100 mg/kg e.g. around 0.01 mg/kg to 40 mg/kg body weight for oral or buccal administration, from around 10 ng/kg to 50 mg/kg body weight for parenteral administration and around 0.05 mg to around 1000 mg e.g. around 0.5 mg to around 1000 mg for nasal administration or administration by inhalation or insufflation.

The compounds of the invention may be prepared by a number of processes as generally described below and more specifically in the Examples hereinafter. In the following process description, the symbols $R^1$, Ar, X, Y, Z, W and U when used in the formulae depicted are to be understood to represent those groups described above in relation to formula (1) unless otherwise indicated. In the reactions described below, it may be necessary to protect reactive functional groups, for example hydroxy, amino, thio or carboxy groups, where these are desired in the final product, to avoid their unwanted participation in the reactions. Conventional protecting groups may be used in accordance with standard practice [see, for example, Green, T. W. in "Protective Groups in Organic Synthesis", John Wiley and Sons, 1991]. In some instances, deprotection may be the final step in the synthesis of a compound of formula (1) and the processes according to the invention described hereinafter are to be understood to extend to such removal of protecting groups.

Thus according to a further aspect of the invention, a compound of formula (1) may be prepared by reaction of a sulphonamide or amide $ArYNH_2$ with a compound of formula (2):

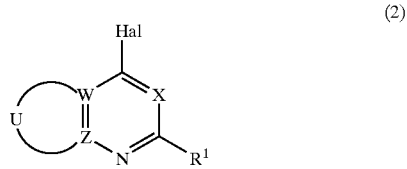

(2)

where Hal is a halogen atom such as a chlorine atom.

The reaction may be performed at an elevated temperature, for exampale the reflux temperature, where necessary in the presence of a solvent, for example a substituted amide such as dimethylformamide, optionally in the presence of a base, for example an inorganic base such as sodium hydride, or most preferably a carbonate such as potassium or caesium carbonate.

Intermediate sulphonamides and amides represented by $ArlYNH_2$ and intermediates of formula (2) are either known compounds or may be obtained by conventional procedures, for example from the known compounds by using one or more of the standard substitution and/or oxidation, reduction or cleavage reactions described below in relation to interconversion of compounds of formula (1).

Thus compounds of formula (1) may also be prepared by interconversion of other compounds of formula (1) and it is to be understood that the invention extends to such interconversion processes. Thus, for example, standard substitution approaches employing for example alkylation, arylation, acylation, thioacylation, sulphonylation, formylation or coupling reactions may be used to add new substitutents to and/or extend existing substituents in compounds of formula (1). Alternatively existing substituents in compounds of formula (1) may be modified by for example oxidation, reduction or cleavage reactions to yield other compounds of formula (1).

The following describes in general terms a number of approaches which can be employed to modify existing Ar and aromatic or heteroaromatic groups represented by groups W, Z and U together in compounds of formula (1). It will be appreciated that each of these reactions will only be possible where one or more appropriate functional groups exist in the compound of formula (1).

Thus, for example alkylation or arylation of a compound of formula (1), for example to introduce a group $-Alk^1(R^3)_n$ or $R^3$ where $R^3$ is an aryl group may be achieved by reaction of the compound with a reagent $(R^3)_nAlk^1L$ or $R^3L$, where L is a leaving group such as a halogen atom, e.g. a bromine, iodine or chlorine atom or a sulphonyloxy group such as an alkylsulphonyloxy, e.g. trifluoromethylsulphonyloxy or arylsulphonyloxy, e.g. phenylsulphonyloxy group. The alkylation or arylation reaction may be carried out in the presence of a base, e.g. an inorganic base such as a carbonate, e.g. caesium or potassium carbonate, an alkoxide, e.g. potassium t-butoxide, or a hydride, e.g. sodium hydride, in a dipolar aprotic solvent such as an amide, e.g. a substitued amide such as diemethylformamide or an ether, e.g. a cyclic ether such as tetrahydrofuran, at around 0° C. to 100° C.

In another general example of an interconversion process, a compound of formula (1) may be acylated or thioacylated, for example to introduce a group $—C(O)R^4$ or $—C(S)R^4$. The reaction may be performed for example with an acyl or thioacyl halide or anhydride in the presence of a base, such as an organic amine e.g. triethylamine or pyridine in a solvent such as an aromatic or halogenated hydrocarbon, e.g. toluene, optionally in the presence of a catalyst, e.g. dimethylaminopyridine dichloromethane at for example ambient up to the reflux temperature, or by reaction with a thioester in an inert solvent such as tetrahydrofuran at a low temperature such as around 0° C.

Compounds of formula (1) may be prepared in another general interconversion reaction by sulphonylation, for example by reaction of the compound with a reagent $R^4S(O)L$ or $R^4SO_2L$ where L is a leaving group as described above in the presence of a base, for example an inorganic base such as sodium hydride in a solvent such as an amide, e.g. a substituted amide such as dimethylformamide at for example ambient temperature. The reaction may in particular be performed with compounds of formula (1) in which Ar and/or X, Y and A together possesses a primary or secondary amino group.

In further examples of interconversion reactions according to the invention compounds of formula (1) may be prepared from other compounds of formula (1) by modification of existing functional groups in the latter.

Thus in one example, ester groups —$CO_2Alk^2$ in compounds of formula (1) may be converted to the corresponding acid [—$CO_2H$] by acid- or base-catalysed hydrolysis depending on the nature of the group $Alk^2$. Acid- or base-catalysed hydrolysis may be achieved for example by treatment with an organic or inorganic acid, e.g. trifluoroacetic acid in an aqueous solvent or a mineral acid such as hydrochloric acid in a solvent such as dioxan or an alkali metal hydroxide, e.g. lithium hydroxide in an aqueous alcohol, e.g. aqueous methanol.

In a second example, —$OR^4$ [where $R^4$ represents an alkyl group such as methyl group] groups in compounds of formula (1) may be cleaved to the corresponding alcohol —OH by reaction with boron tribromide in a solvent such as a halogenated hydrocarbon, e.g. dichloromethane at a low temperature, e.g. around −78° C.

In another example, alcohol —OH groups in compounds of formula (1) may be converted to a corresponding —$OR^4$ group by coupling with a reagent $R^4OH$ in a solvent such as tetrahydrofuran in the presence of a phosphine, e.g. triphenylphosphine and an activator such as diethyl-, diisopropyl-, or dimethylazodicarboxylate.

Aminosulphonylamino [—$NHSO_2NH_2$] groups in compounds of formula (1) may be obtained, in another example, by reaction of a corresponding amine [—$NH_2$] with sulphamide in the presence of an organic base such as pyridine at an elevated temperature, e.g. the reflux temperature.

In another example of an interconversion reaction, amine (—$NH_2$) groups may be alkylated using a reductive alkylation process employing an aldehyde and a borohydride, for example sodium triacetoxyborohyride or sodium cyanoborohydride, in a solvent such as a halogenated hydrocarbon, e.g. dichloromethane, a ketone such as acetone, or an alcohol, e.g. ethanol, where necessary in the presence of an acid such as acetic acid at around ambient temperature.

In a further example, amine [—$NH_2$] groups in compounds of formula (1) may be obtained by hydrolysis from a corresponding imide by reaction with hydrazine in a solvent such as an alcohol, e.g. ethanol at ambient temperature.

In another example, a nitro [—$NO_2$] group may be reduced to an amine [—$NH_2$], for example by catalytic hydrogenation using for example hydrogen in the presence of a metal catalyst, for example palladium on a support such as carbon in a solvent such as an ether, e.g. tetrahydrofuran or an alcohol e.g. methanol, or by chemical reduction using for example a metal, e.g. tin or iron, in the presence of an acid such as hydrochloric acid.

In a further example, amide [—$CONHR^4$] groups in compounds of formula (1) may be obtained by coupling a corresponding acid [—$CO_2H$] or an active derivative thereof, e.g. an acid anhydride, ester, imide or halide, with an amine $R^4NH_2$. The coupling reaction may be performed using standard conditions for reactions of this type. Thus for example the reaction may be carried out in a solvent, for example an inert organic solvent such as an amide, e.g. a substituted amide such as dimethylformamide, at a low temperature, e.g. −30° C. to ambient temperature, optionally in the presence of a base, e.g. an organic base such as a cyclic amine, e.g. N-methylmorpholine, and where necessary in the presence of a condensing agent, for example a diimide such as 1-(3-dimethylaminopropyl)-3-ethylcarbodiimide, advantageously in the presence of a catalyst such as a N-hydroxytriazole, e.g. 1-hydroxybenzotriazole.

Aromatic halogen substituents in compounds of the invention may be subjected to halogen-metal exchange with a base, for example a lithium base such as n-butyl or t-butyl lithium, optionally at a low temperature, e.g. around −78° C., in a solvent such as tetrahydrofuran and then quenched with an electrophile to introduce a desired substituent. Thus, for example, a formyl group may be introduced by using dimethylformamide as the electrophile; a thiomethyl group may be introduced by using dimethyidisulphide as the electrophile.

In another example, sulphur atoms in compounds of the invention may be oxidised to the corresponding sulphoxide using an oxidising agent such as a peroxy acid, e.g. 3-chloroperoxybenzoic acid, in an inert solvent such as a halogenated hydrocarbon, e.g. dichloromethane, at around ambient temperature.

In a further example of an interconversion reaction, a compound of the invention containing a substituent $R^2$ in which $R^2$ is an aryl or heteroaryl group may be prepared by coupling a corresponding compound in which the $R^2$ substituent is a halogen atom such as a bromine atom, with a boronic acid $Ar^1B(OH)_2$ [in which $Ar^1$ is an aryl or heteroaryl group as defined above for Ar] in the presence of a complex metal catalyst.

Suitable catalysts include heavy metal catalysts, for example palladium catalysts such as tetrakis(triphenylphosphine) palladium. The reaction may be performed in an inert organic solvent, for example an ether such as dimethoxyethane, in the presence of a base, e.g. an alkali carbonate such as sodium carbonate, at an elevated temperature, e.g. the reflux temperature.

N-oxides of compounds of formula (1) may be prepared for example by oxidation of the corresponding nitrogen base using an oxidising agent such as hydrogen peroxide in the presence of an acid such as acetic acid, at an elevated temperature, for example around 70° C. to 80° C., or alternatively by reaction with a peracid such as peracetic acid in a solvent, e.g. dichloromethane, at ambient temperature.

The following Examples illustrate the invention.
All temperatures are in ° C.
The following abbreviations are used:

DEAD - Diethyl azodicarboxylate;
EtOAc - ethyl acetate;
DCM - dichloromethane;
MeOH - methanol;
LCMS - liquid chromatography mass spectroscopy.
THF - tetrahydrofuran;
RT - retention time;
DMF - dimethylformamide;

All NMR's were obtained at 300 MHz, unless otherwise indicated.

EXAMPLE 1

4-Bromo-N-(6,7-dimethoxyquinazolin-4-yl)benzenesulphonamide

To a suspension of sodium hydride [60% dispersion in oil] (135 mg, 6.6 mmol) in dry DMF (10 ml) under a nitrogen atmosphere at 0° C. was added benzenesulphonamide (0.78 g, 3.3 mmol) and the mixture stirred with warming to ambient temperature over 0.5 h. To this mixture was added 4-chloro-6,7-dimethoxyquinazoline (0.75 g, 3.3 mmol) and the reaction temperature was raised to 80° for 12 h. The reaction was poured onto 80 ml ice-water adjusted to pH 5 with 2 M hydrochloric acid. The resulting precipitate was collected by filtration and dried before being subjected to column chromatography [SiO$_2$; 20–60% EtOAc-hexane] to give the title compound (110 mg) as a white solid. M.p. 241–242°.δH (d$^6$ DMSO) 8.34 (1H, s), 7.90 (2H, d, J 8.5 Hz), 7.73 (2H, d, J 8.5 Hz), 7.50 (1H, s), 7.13 (1H, s), 3.93 (3H, s) and 3.89 (3H, s).

EXAMPLE 2

2-Chloro-N-(6,7-dimethoxyquinazolin-4-yl) benzenesulphonamide

From 2-chlorobenzenesulphonamide (0.63 g, 3.3 mmol), 4-chloro-6,7-dimethoxyquinazoline (0.75 g, 3.3 mmol) and sodium hydride [60%] (135 mg, 6.6 mmol) to give the title compound (37 mg) as a white solid M.p.>270° (decomp.). δH (CDCl3) 8.26 (1 H, dd, J 6.7, 0.8 Hz), 8.11 (1 H, s), 7.59 (1H, s), 7.51–7.33 (4H, m), 7.14 (1H, s), 4.01 (3H, s) and 3.93 (3H, s).

EXAMPLE 3

3-Chloro-N-(6,7-dimethoxyquinazolin-4-yl) benzenesulphonamide

From 3-chlorobenzenesulphonamide (0.63 g, 3.3 mmol), 4-chloro-6,7-dimethoxyquinazoline (0.75 g, 3.3 mmol) and sodium hydride [60%] (135 mg, 6.6 mmol) to give the title compound (9 mg) as a white solid. M.p. 186–188°. δH (d$^6$-DMSO) 8.35 (1H, s), 7.97 (1H, s), 7.89 (1H, d, J 7.6 Hz), 7.62–7.52 (2H, m), 7.50 (1H, m), 7.12 (1H, s), 3.92 (3H, s) and 3.89 (3H, s).

EXAMPLE 4

4-Chloro-N-(6,7-dimethoxyquinazolin-4-yl) benzenesulphonamide

From 4-chlorobenzenesulphonamide (0.63 g, 3.3 mmol), 4-chloro-6,7-dimethoxyquinazoline (0.75 g, 3.3 mmol) and sodium hydride [60%] (135 mg, 6.6 mmol) to give the title compound (7 mg) as a white solid. M.p. 228–230°. δH (CDCl$_3$) 8.06 (1H, s), 7.94 (2H, d, J 8.8 Hz), 7.61 (1H, s), 7.46 (2H, d, J 8.8 Hz), 7.14 (1H, s), 4.02 (3H, s) and 3.98 (3H, s).

EXAMPLE 5

N-(6,7-Dimethoxyquinazolin-4-yl)-4-methoxy benzenesulphonamide

From 4-methoxybenzenesulphonamide (0.62 g, 3.3 mmol), 4-chloro-6,7-dimethoxyquinazoline (0.75 g, 3.3 mmol) and sodium hydride [60%] (135 mg, 6.6 mmol) to give the title compound (40 mg) as a white solid. M.p.>240°. δH (d$^6$ DMSO) 8.30 (1H, s), 7.92 (2H, d, J 8.9 Hz), 7.50 (1H, s), 7.16 (1H, s), 7.04 (2H, d, J 8.9 Hz), 3.92 (3H, s), 3.87 (3H, s) and 3.79 (3H, s).

EXAMPLE 6

N-(6,7-Dimethoxyquinazolin-4-yl)4-methylbenzene sulphonamide

From 4-methoxybenzenesulphonamide (0.56 g, 3.3 mmol), 4-chloro-6,7-dimethoxyquinazoline (0.75 g, 3.3 mmol) and sodium hydride [60%] (135 mg, 6.6 mmol) to give the title compound (8 mg) as a white solid. M.p.>250°. δH (CDCl$_3$) 8.08 (1H, s), 7.92 (2H, d, J 8.4 Hz), 7.63 (1H, s), 7.27 (2H, d, J 8.4 Hz), 7.12 (1H, s), 4.02 (3H, s) and 3.98 (3H, s).

EXAMPLE 7

N-(6,7-dimethoxyquinazolin-4-yl)-2-iodobenzene sulphonamide

From 2-iodobenzenesulphonamide (0.61 g, 2.0 mmol), 4-chloro-6,7-dimethoxyquinazoline (0.4 g, 2.0 mmol) and sodium hydride (60%) (80 mg, 2.0 mmol) to give the title compound (26 mg) as white crystals. LCMS (ES$^+$, 70 eV): m/z 4712 (M+H)$^+$ RT 3.14 min.

EXAMPLE 8

2-Cyano-N-(6,7-dimethoxyquinazolin-4-yl)benzene sulphonamide

From 2-cyanobenzenesulphonaomide (0.40 g, 2.0 mmol), 4-chloro-6,7-dimethoxyquinazoline (0.4 g, 2.0 mmol) and sodium hydride (60%) (80 mg, 2.0 mmol) to give the title compound (5.6 mg) as white crystals. LCMS (ES$^+$, 70 eV): m/z 372 (M+H)$^+$, RT=2.92 min.

EXAMPLE 9

2-Bromo-N-(6,7-dimethoxyquinazolin-4-yl)benzene sulphonamide

From 2-bromobenzenesulphonamide (0.5 g, 2.0 mmol), 4-chloro-6,7-dimethoxyquinazoline (0.4 g, 2.0 mmol) and sodium hydride (60%) (80 mg, 2.0 mmol) to give the title compound (15 mg) as white crystals. LCMS (EC$^+$, 70 eV): m/z 425 (M+H)$^+$, RT=3.13 min.

Biological Activity

The following assays were used to demonstrate the activity and selectivity of compounds according to the invention:

KDR Kinase and FGFr2 Kinase

The activities of recombinant KDR kinase and FGFr2 kinase were determined by measuring their ability to transfer the γ-phosphate from [$^{33}$P]ATP to polyglutamic acid-tyrosine (pEY).

The assay methodology employed for both kinases is identical except that in the assay of KDR kinase the diluent used throughout was 20 mM HEPES pH 7.25 containing 2 mM MnCl$_2$, 2 mM MnCl$_2$, 5 mM DTT and 0.05% Brij 35, whereas in the FGFr2 assay 10 mM MnCl$_2$ is used instead of 2 mM MnCl$_2$ and 2 mM MnCl$_2$.

The assay was conducted in a total volume of 202 μl containing 1–10 ng kinase, 5 μg/ml pEY (4:1) (Sigma, UK), 1 μM ATP (containing ~50,000 cpm [$^{33}$P]ATP (Amersham International, UK) (Sigma, UK) and test inhibitors at the appropriate concentration. The test inhibitors were dissolved in DMSO and added such that the final concentration of DMSO in the assay did not exceed 2% (v/v). The assay was initiated by addition of kinase and terminated after 10 minutes incubation at room temperature by addition of 50 μl of 20 mM HEPES pH 7.25 containing 0.125 M EDTA and 10 mM ATP. A 200 μl aliquot was applied to the well of a Millipore (UK) MAFC filter plate containing 100 μl of 30% (w/v) trichloroacetic acid (TCA). The plate was then placed on a suitable manifold and connected to a vacuum. After complete elimination of the liquid each well was washed under vacuum using five volumes (100 μl per wash) of 10% (w/v) TCA and finally two volumes (100 μl per wash) of ethanol. The bottom of the filter plate was then sealed and 100 μl per well of Ultima Gold (Beckham, UK) scintillant was added to each well. The readioactivity was measured using an appropiate scintillation counter such as a Wallac Trilux or Packard TopCount. The IC$_{50}$ value for each inhibitor was obtained from log dose inhibition curves fitted to the four-parameters logistic equation.

p56$^{Ick}$ Kinase

The tyrosine kinase activity of p56$^{Ick}$ was determined using a RR-src peptide (RRLIEDNEYTARG) and [γ-$^{33}$P] ATP as substrates. Quantitation of the $^{33}$P-phosphorylated peptide formed by the action of p56$^{Ick}$ was achieved using an adaption of the method of Geissler et al (J. Biol. Chem. (1990) 265, 22255–22261).

All assays were performed in 20 mM HEPES pH 7.5 containing 10 mM MgCl$_2$, 10 mM MnCl$_2$, 0.05% Brij, 1 μM ATP (0.5 μCi[γ-$^{33}$P]ATP) and 0.8 mg/ml RR-src. Inhibitors in dimethylsulphoxide (DMSO) were added such that the final concentration of DMSO did not exceed 1%, and enzyme such that the consumption of ATP was less than 10%. After incubation at 30° C. for 15 min, the reaction was terminated by the addition of one-third volume of stop reagent (0.25 mM EDTA and 33 mM ATP in dH$_2$O). A 15 μl aliquot was removed, spotted onto a P-30 filtermat (Wallac, Milton Keynes, UK), and washed sequentially with 1% acetic acid and de-ionised water to remove ATP. The bound $^{33}$P-RR-src was quantitated by scintillation counting of the filtermat in a Betaplate scintillation counter (Wallac, Milton Keynes, UK) after addition of Meltilex scintillant (Wallac, Milton Keynes, UK).

The dpm obtained, being directly proportional to the amount of $^{33}$P-RR-src produced by p56$^{Ick}$, were used to determine the IC$_{50}$ for each compound. The IC$_{50}$ was defined as the concentration of compound required to reduce the production of $^{33}$P-RR-src by 50%.

EGFr Kinase

The tyrosine kinase activity of the EGF receptor (EGFr) was determined using a similar methodology to the p56$^{Ick}$ kinase assay, except that the RR-src peptide was replaced by a peptide substrate for EGFr obtained from Amersham International plc (Little Chalfont, UK) and used at the manufacturer's recommended concentration. IC$_{50}$ values were determined as described previously in the p56$^{Ick}$ assay.

Protein Kinase C Assay

Inhibitor activity against protein kinase C (PKC) was determined using PKC obtained from Sigma Chemical Company (Poole, UK) and a commercially available assay system (Amersham International plc, Amersham, UK). Briefly, PKC catalyses the transfer of the γ-phosphate ($^{32}$P) of ATP to the threonine group on a peptide specific for PKC.

Phosphorylated peptide is bound to phosphocellulose paper and subsequently quantified by scintillation counting. The inhibitor potency is expressed as either (i) the concentration required to inhibit 50% of the enzyme activity (IC$_{50}$) or (ii) the percentage inhibition achieved by 10 μM inhibitor.

In these tests, compounds of the invention have IC$_{50}$ values in the EGFr kinase assay of around 1 μM and below. In contrast, in the other assays described, the same compounds had IC$_{50}$ values in each assay of greater than 10 μM. In each instance the compound clearly had potent and selective EGFR kinase inhibitory action.

The invention claimed is:

1. A compound of formula (1a)

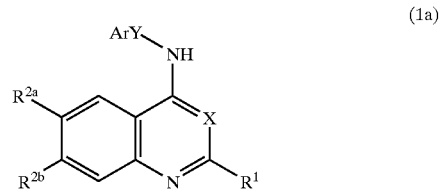

(1a)

wherein
Ar is an aryl or heteroaryl group;
Y is a —S(O$_2$)— group;
R$^1$ is a hydrogen or halogen atom or an alkyl, haloalkyl, alkoxy or haloalkoxy group;
X is a nitrogen atom; and
R$^{2a}$ and R$^{2b}$, which may be the same or different, are each a C$_{1-6}$alkoxy group; or a salt, solvate, hydrate, or N-oxide thereof.

2. A compound which is:
2-Bromo-N-(6,7-dimethoxyquinazolin-4-yl)benzenesulphonamide;
N-(6,7-Dimethoxyquinazolin-4-yl)-2-iodobenzenesulphonamide;
2-Cyano-N-(6,7-dimethoxyquinazolin-4-yl)benzenesulphonamide;
4-Bromo-N-(6,7-dimethoxyquinazolin-4-yl)benzenesulphonamide;
2-Chloro-N-(6,7-dimethoxyquinazolin-4-yl)benzenesulphonamide;
3-Chloro-N-(6,7-dimethoxyquinazolin-4-yl)benzenesulphonamide;
4-Chloro-N-(6,7-dimethoxyquinazolin-4-yl)benzenesulphonamide;
N-(6,7-Dimethoxyquinazolin-4-yl)-4-methoxybenzenesulphonamide;
N-(6,7-Dimethoxyquinazolin-4-yl)-4-methylbenzenesulphonamide;
or a salt, solvate, and hydrate thereof.

3. A pharmaceutical composition comprising a compound according to claim 1 together with one or more pharmaceutically acceptable carriers, excipients or diluents.

4. A method for treating psoriasis comprising administering to a mammal suffering from psoriasis a therapeutically effective amount of a compound according to formula (1a):

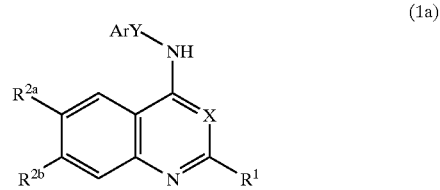

(1a)

wherein:

Ar is an aryl or heteroaryl group;

Y is a —S(O$_2$)— group;

X is a nitrogen atom;

R$^1$ is a hydrogen or halogen atom or an alkyl, haloalkyl, alkoxy or haloalkoxy group; and R$^{2a}$ and R$^{2b}$, which may be the same or different, are each a C$_{1-6}$alkoxy group; or a salt, solvate, hydrate, or N-oxide thereof.

* * * * *